(12) United States Patent
Dundale et al.

(10) Patent No.: US 7,033,990 B2
(45) Date of Patent: Apr. 25, 2006

(54) COMPOSITIONS ABLE TO INDICATE WHEN THEY BECOME INEFFICIENT IN USE

(75) Inventors: Jeffrey Dundale, Hamilton, NJ (US); Jana Pika, Princeton, NJ (US)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 10/438,936

(22) Filed: May 16, 2003

(65) Prior Publication Data

US 2003/0207787 A1 Nov. 6, 2003

Related U.S. Application Data

(63) Continuation of application No. PCT/IB01/02137, filed on Nov. 14, 2001, which is a continuation-in-part of application No. 09/729,241, filed on Dec. 5, 2000, now abandoned.

(51) Int. Cl.
*A61K 7/46* (2006.01)

(52) U.S. Cl. ............................................. 512/1; 252/1

(58) Field of Classification Search .................... 252/1; 512/1

See application file for complete search history.

(56) References Cited

U.S. PATENT DOCUMENTS

| | | | |
|---|---|---|---|
| 4,128,508 A * | 12/1978 | Munden | 512/1 |
| 4,824,827 A * | 4/1989 | Kelly et al. | 512/1 |
| 5,019,434 A * | 5/1991 | Matsumoto | 428/35.7 |
| 5,419,879 A * | 5/1995 | Vlahakis et al. | 422/305 |
| 5,501,945 A | 3/1996 | Kannakkanatt | 430/338 |
| 6,706,761 B1 * | 3/2004 | Bublitz et al. | 514/531 |
| 6,790,670 B1 * | 9/2004 | Munagavalasa et al. | 436/164 |

FOREIGN PATENT DOCUMENTS

| | | |
|---|---|---|
| DE | 26 39 851 A | 3/1977 |
| EP | 0 309 173 A2 | 3/1989 |
| EP | 0 567 018 A2 | 4/1992 |
| JP | 62 281802 | 12/1987 |
| JP | 3 199964 A | 12/1989 |
| JP | 06 122863 | 4/1994 |
| JP | 07 145299 A | 10/1995 |
| WO | WO 00/24434 | 4/2000 |

* cited by examiner

*Primary Examiner*—Monique T. Cole
(74) *Attorney, Agent, or Firm*—Winston & Strawn LLP

(57) ABSTRACT

The invention concerns a composition capable of indicating by color change when consumer articles, particularly volatile material dispensers, containing or associated with the composition have become inefficient in use. The composition includes: a) a volatile liquid component, b) a non-volatile component of an oxide or hydroxide of the metals of group III or IV of the periodic table and a polymer obtainable by the reaction, in the presence of the volatile liquid component, of a functionalized polymer with a cross-linking, and c) a dye capable of changing color as a function of the medium in which it is incorporated. Optionally, the composition can also contain an effective amount of an acidic compound. The invention also concerns the consumer article containing the composition, in particular a device aimed to diffuse a volatile or partially volatile liquid, more specifically an air freshener.

21 Claims, No Drawings

COMPOSITIONS ABLE TO INDICATE WHEN THEY BECOME INEFFICIENT IN USE

CROSS-REFERENCE TO RELATED APPLICATIONS

This application is a continuation of International Application PCT/IB01/02137 filed Nov. 14, 2001, the content of which is expressly incorporated herein by reference thereto, and a continuation-in-part of U.S. application Ser. No. 09/729,241 filed Dec. 5, 2000, now abandoned.

FIELD OF THE INVENTION

The invention concerns a composition capable of indicating by color change when consumer articles, particularly volatile material dispensers, associated with said composition, have become inefficient in use.

The composition comprises:
a) a volatile liquid component,
b) a non-volatile component selected from the group consisting of the oxides and hydroxides of the metals in group III or IV of the periodic table and a polymer obtainable by the reaction, in the presence of the volatile liquid component, of
  i) a polymer such as maleinized polybutadiene, maleinized polyisoprene, or a copolymer of ethylene and maleic anhydride, with
  ii) a cross-linking agent having one or more complementary functional groups; and
c) a dye capable of changing color as a function of the medium in which it is incorporated. Optionally, the composition can also contain an acidic compound.

The invention also concerns the consumer article containing, or associated with, said composition, in particular a device intended to diffuse a volatile liquid, more specifically an air freshener.

BACKGROUND OF THE INVENTION

The use of compositions able to indicate, by changing their color, the loss of efficiency of a consumer article with which the compositions are associated, is quite wide. The usefulness of such compositions is quite apparent, as they allow the visual assessment of the right moment at which the consumer article needs to be renewed.

The known compositions are used in consumer articles such as air fresheners (e.g. see S. C. Johnson, EP 0309173 A2), packaging films (e.g. see University of Akron, U.S. Pat. No. 5,501,945) or coating films (e.g. see Nippon Photograph Printing, JP 03199964).

In general, changes occurring in a consumer article during its use or storage, induce the compositions to respond, and therefore to change color, indicating the loss of efficiency. The most commonly occurring variations include pH, redox potential, solvent, pressure or light irradiation changes.

European application EP 309173 A2 discloses the use of a homogeneous indicator composition that includes a volatilizable non-aqueous solvent, a soluble polar indicator dye and a soluble proton donating compound. During the evaporation of the volatilizable non-aqueous solvent, the concentration of the proton donating compound progressively increases, thus inducing a gradual pH change, the latter producing a gradual color change indicating the lost of efficiency. A limitation of such a composition comes from the fact that the preferred proton donors are liquid and therefore must be less volatile than the solvent in order to ensure the functioning of the composition. A further serious drawback of such a composition comes from the fact that the color change, and therefore the information provided to the consumer concerning the efficiency of the article, occurs only gradually and is spread out through the useful life of the article. This gradual change makes it difficult to assess when the article has effectively become inefficient in use.

The Japanese document JP 03199964 discloses a printable coating film for discoloration in the course of time, formed by an ink containing a powder of (hydro)oxides, a dye, a solvent that has at least one oxygen atom in its formula and a resin for the binder as essential components. In said film, the evaporation of the solvent induces the color change.

In order to achieve a good matching between the rate of evaporation of the solvent and the effective life of the associated article, the realization of an efficient film is complex and requires a very careful dosing of the quantity of solvent and of the thickness of the film. Furthermore, as above, the main weakness consists in the fact that the color change is a gradual one, as clearly stated by the authors.

Despite prior known compositions aimed at indicating when consumer articles have become inefficient in use, there is still a need for compositions which are of simple preparation and able to provide an unambiguous indication of the consumer article status through a clear and unambiguous color change.

SUMMARY OF THE INVENTION

The present invention relates to a composition of simple preparation and capable of indicating by a clear and unambiguous color change when a consumer article containing, or associated with, said composition has become ineffective in use. As consumer articles, volatile material dispensers are particularly intended.

The composition of the invention comprises:
a) a volatile liquid component,
b) a non-volatile component selected from the group consisting of the oxides and hydroxides of the metals in group III or IV of the periodic table and a polymer obtainable by the reaction, in the presence of the volatile liquid component, of
  i) a functionalized polymer selected from the group consisting of a functionalized liquid polymer, such as maleinized polybutadiene or maleinized polyisoprene, and a copolymer of ethylene and maleic anhydride, with
  ii) a cross-linking agent having one or more complementary functional groups; and
c) a dye capable of changing color as a function of the medium in which it is incorporated. Optionally, the composition can also contain an acidic compound.

In the composition of the invention the dye is initially and essentially dissolved in the volatile liquid component.

DETAILED DESCRIPTION OF THE PREFERRED EMBODIMENTS

The volatile liquid component will be preferably composed essentially of a volatile material that is intended to be dispersed into the surrounding air by the consumer article with which the composition of the invention is associated. The volatile liquid component will be a non-aqueous liquid, more preferably a low polarity liquid, in order to allow the dye, once dissolved in said volatile liquid component, to be colorless or to adopt a color clearly distinct from the color that said dye assumes when deposited on the non-volatile component. By non-aqueous liquid it is intended a liquid containing less that 1% of water.

As the volatile liquid component, there can be used for example perfumes, in which case the consumer product will be of the air freshener type. Other suitable volatile liquid phases can be a deodorizing or sanitizing agent or an insect repellent or any other volatile material capable of imparting perceptible and desirable benefits to the quality of the air into which it is diffused.

As the perfume or perfuming ingredients there can be used any ingredient or mixture of ingredients currently used in perfumery. The latter can be made of discreet chemicals; more often, however, it will be a more or less complex mixture of volatile ingredients of natural or synthetic origin. The nature of these ingredients can be found in specialized books of perfumery, e.g. in S. Arctander (Perfume and Flavor Chemicals, Montclair N.J., USA 1969) or similar textbooks of reference, and a more detailed description thereof is not warranted here.

Although special mention has been made herein above of the perfuming effect that can be exerted by the compositions of the invention, the same principles apply to the manufacture of analogous compositions for the diffusion of deodorizing or sanitizing vapors, the perfume base being replaced by a deodorizing composition, a bactericide, an insecticide, an insect repellent or an insect attractant. By the term "sanitizing vapors", we refer here not only to the vapors of those substances which can enhance the degree of acceptance of the air surrounding the observer, but also to those substances which can exert an attractant or repellent effect toward certain species of insects, for instance toward houseflies or mosquitoes, or else, which can have bactericide or bacteriostatic activity. It goes without saying that mixtures of such agents can also be used.

A person skilled in the art of preparing a volatile liquid component, as herein above defined, will be perfectly able to choose the ingredients, as well as their concentrations, needed for the manufacture of a volatile liquid component imparting the desired benefits and, at the same time, allowing the dye, once dissolved in, to be colorless or to adopt a color clearly distinct from the color that said dye assumes when deposited on the non-volatile component.

As previously mentioned, the non-volatile component is a metal oxide or hydroxide of the metals in group III or IV of the periodic table or yet some specific polymers. These polymers correspond in fact to the polymers used in the formulation of the anhydrous polymer gels disclosed in the U.S. Pat. No. 5,780,527 or in the application WO 00/24434, and the relevant parts of said documents form part of the present application and are incorporated herein by reference.

In a preferred embodiment of the invention composition, the non-volatile component will be silica gel, alumina and FLORISIL® ($MgSiO_4$; origin: Supelco).

In an equally preferred embodiment of the invention composition, the non-volatile component will be the polymers used in the formulation of the anhydrous polymer gels disclosed in U.S. Pat. No. 5,780,527 or in WO 00/24434.

The polymers used in the formulation of the anhydrous polymer gels disclosed in U.S. Pat. No. 5,780,527, or in WO 00/24434, are able to form gels capable of absorbing large amounts of the volatile liquid component. These polymers are obtained via the cross-linking reaction between a functionalized polymer and a suitable cross-linking agent, in the presence of the volatile liquid component.

Preferably, and as non-limiting examples, the functionalized polymer is a functionalized liquid polymer selected from the group consisting of maleinized polyisoprene of molecular weight 200000–500000 or maleinized polybutadiene of molecular weight 5000–20000, especially those known under the trademark LITHENE®, such as LITHENE® N4-B-10MA or LITHENE® N4–9000 10MA [origin: Revertex Ltd]; 9000 stands for the molecular weight of polybutadiene before maleinization, whilst 10 MA indicates the degree of maleinization–in this case 10 parts of maleic anhydride per 100 parts of polybutadiene (=about 9.1%).

As non-limiting examples, the cross-linking agent is selected from the group consisting of a dihydroxypolybutadiene, an ethoxylated primary amine, an alkylpropyldiamine having an ethoxylated higher aliphatic chain, an alkylpropyldiamine having a propoxylated higher aliphatic chain, diethanolamine, diethylenetriamine, a polyoxy-alkylenediamine or -triamine, and a cocoamine having 5 ethylene oxide units. More preferably, and as non-limiting examples, the cross-linking agent is selected from the group consisting of an oleylamine having 2 ethylene oxide units per molecule, such as those known under the trademark CRODAMET® O2 (origin: Croda Chemicals Ltd), a cocoamine having 5 ethylene oxide units per molecule, such as those known under the trademark CRODAMET® C5, and a polyoxy-alkylenediamine or -triamine, such those known under the trademark JEFFAMINE® (origin: Huntsman Corporation).

From the above description of the volatile and non-volatile components of the invention compositions, it is understood that said compositions are biphasic. By the term biphasic is intended a liquid-solid system (e.g., in the case of a composition containing the liquid volatile and a metal oxide) or a gel system wherein the liquid volatile phase is dispersed into the polymer phase (e.g., in the case of a composition containing the liquid volatile and a polymer such as herein above mentioned).

The dyes are a key component of the composition. As mentioned above, a dye useful for the composition according to the invention must be capable of color change as a function of the medium in which it is incorporated. In other words, the dye must be able to adopt a different color according whether said dye is dissolved into the volatile liquid component or deposited on the non-volatile component. Preferably the dye, when dissolved in the volatile liquid component, is colorless or has a color clearly distinct from the color that said dye assumes when deposited on the non-volatile component.

Additionally, suitable dyes are such that their affinity for the volatile liquid phase is higher than for the non-volatile component; e.g. the dye will be preferably dissolved in the volatile liquid component rather than deposited on the non-volatile component. The relative affinity of the dye for the two components will determine the fragrance depletion point at which the color change will appear. The higher the affinity of the dye for the volatile liquid component, compared to the affinity for the non-volatile component, the higher will be the depletion of fragrance when the color change appears.

By the expression "depletion of fragrance" we mean the percentage of volatile liquid component which has been released into the air surrounding the consumer article containing the composition of the invention.

As the dye, any current such substance may be employed, provided that it satisfies the criteria cited herein above. As non-limiting examples, suitable dyes are selected from the compounds of the diaryl phthalide family and their indole derivatives, the compounds of the diaryl sulphophthalein family, or from the compounds of the fluoran family.

Preferred dyes are N-[9-(2-carboxyphenyl)-6-(diethylamino)-3H-xanthen-3-ylidene]-N-ethylethamine free base commonly known as Rhodamine B base, 3,3-bis(1-octyl-2-methylindol-3-yl) phthalide, also known as PERGASCRIPT® Red I-6B (origin CIBA SC Switzerland), 3,3-bis (1-ethyl-2-methylindol-3-yl) phthalide, 3,3-bis(1-butyl-2-methylindol-3-yl) phthalide, 3,3-bis(1-pentyl-2-methylindol-3-yl) phthalide, 3,3-bis(4-dimethylaminophenyl)-6-dimethyl amino phthalide, commonly referred to as crystal violet lactone, 2'-(bisphenylmethyl) amino-6-(diethylamino) spiro-(isobenzofuran-1 (3H),9'-(9H) xanthen)-3-one also known as malachite green lactone, 3-(4-diethylamino) phenyl-3-(di(4-octyl) phenylamino) 1-(3H)-isobenzofuran-3-one and 2-anilino-3-methyl-6-diethyl-amino fluoran.

Moreover, in order to fine tune the moment at which the color change occurs, it is possible to add to the invention composition an acidic compound. However as already mentioned, said acidic compound is an optional constituent of the composition.

Said optional fourth constituent can be a liquid or solid compound, but it shall in any case be less volatile than the volatile liquid component. The acidic compound can be selected from the group constituted by the chemicals containing at least a proton donating group such as a carboxylic acid or a hydroxyl group. Preferred acidic materials are lauric, stearic, myristic, palmitic acid or diphenol-dimethylmethane.

The above-identified constituents of the composition, which is an object of the invention, can be admixed in various ratios depending on the nature of the different constituents.

One can cite, as non-limiting examples and for all types of consumer articles associated with said composition, compositions wherein: a) the dye is present in an amount comprised between 0.007% and 2%; b) the non-volatile component is present in an amount comprised between 0.5% and 12%; c) the acidic compound is present in an amount comprised between 0% and 20%; and d) the volatile liquid component constitutes the balance of the composition, percentage being relative to the weight of the composition. However in the case the non-volatile component is a polymer as previously defined, it is possible to increase the quantity of said constituent up to 35% of the composition weight.

Preferably compositions wherein: a) the dye is present in an amount comprised between 0.01% and 0.5%; b) the non-volatile component is present in an amount comprised between 1% and 10%; c) the acidic compound is present in an amount comprised between 0% and 5%; and d) the volatile liquid component constitutes the balance of the composition, percentage being relative to the weight of the composition. In the case the non-volatile component is a polymer, it is possible to increase the quantity of said constituent up to 25% of the composition weight.

Naturally, it is clear to a person skilled in the art that the various components can be admixed in any quantity required to achieve the color change at the desired fragrance depletion point of the article to which they are associated.

As anticipated above, the composition of the invention can be contained in, or associated with, a consumer article, whereby as a consumer article it is intended here more specifically a volatile material dispenser. These consumer articles are also embodiments of the present invention.

Such a volatile material dispenser can be, depending on the nature of the liquid component used in the preparation of the composition, a perfuming or sanitizing device such as an air freshener, particularly of the solid or membrane type, a diaper pail freshener, a car freshener, a closet freshener, a cat litter box freshener, a shoe freshener or a garbage pail freshener, an insecticide or an insect repellent device.

In fact, a container and an adequate composition of the invention will compose said consumer article. The composition will be housed by the container and at least a portion of the container surface will allow the escape of the vapors of the volatile liquid component into the air surrounding said consumer article. The container can be made of any material usable for this kind of consumer article. Naturally said material must be chemically inert toward the composition of the invention.

During storage, the container, in which the invention composition lies, is sealed, in order not to allow diffusion of the volatile liquid phase into the surroundings. The consumer will then activate the consumer article simply by removing the seal, after which the volatile liquid phase will start to diffuse into the surrounding air. Once the volatile liquid phase has evaporated to such an extent that its desired action (e.g. perfuming or insect repellent) starts to fade or has faded to a certain extent, the composition of the invention will change its color, and not before. This technical effect will provide the consumer with clear and unambiguous information concerning the efficiency in use of the article.

Preferred consumer articles are an air freshener operating at room temperature, such as a solid or a gel type air freshener, or in a small oven, such as a membrane type "plug-in" air freshener.

We have also found that in the case of a membrane type "plug-in" air freshener the most convenient compositions are those containing between 1 and 10%, relative to the weight of the composition, of silica or alumina as non-volatile component.

In the case of a gel type air freshener the most convenient compositions are those containing between 13 and 25%, relative to the weight of the composition, of a polymer used in the formulation of the anhydrous polymer gels disclosed in U.S. Pat. No. 5,780,527 as non-volatile component.

EXAMPLES

The invention will now be described in further detail by way of the following examples.

Example 1

Tuning of the Depletion Point of a Composition According to the Invention as a Function of Dye Concentration An air freshener composition has been prepared by mixing the following ingredients in the indicated amounts:

| Ingredients | Parts by weight |
| --- | --- |
| Amorphous fumed silica gel[1] | 4 |
| Lauric acid | according to table 1 |
| PERGASCRIPT RED I-6B ®[2] | according to table 1 |
| Fragrance[3] | 95.5[1] |
| | 100 |

[1]up to 95.5% of the weight of the total composition, the exact quantity constitutes the balance of the composition
[1]Grade PTG; origin: Cabot Corp., USA
[2]Origin: Ciba SC, Switzerland -continued 3) The fragrance was prepared by admixing the following ingredients:

| Ingredients | Parts by weight |
|---|---|
| Benzyl acetate | 15 |
| Citronellyl acetate | 5 |
| Linalyl acetate | 10 |
| Dihydromyrcenol | 10 |
| 3-(3-methoxypropoxy)-1-propanol | 15 |
| Linalool | 5 |
| LORYSIA ®a) | 10 |
| Phenethylol | 10 |
| Orange terpenes | 10 |
| Verdox | 10 |
| | 100 | a) 4-(1,1-dimethylethyl)-1-cyclohexyl acetate; origin: Firmenich SA (Geneva, Switzerland)

Then, 0.25 g of the composition were placed on a 7 cm x 7 cm cut piece of aluminum foil. The initial weight of the solution was measured. The solution on aluminum foil was placed in a 55° C. incubator to increase the depletion rate of the fragrance. The sample was observed for any color change every 30 minutes. Once the color change was observed, the sample was then weighed, and the percentage of fragrance depletion calculated.

TABLE 1

Influence of the dye/acid concentration on the depletion point of a composition at the moment of the color change of the composition:

| Parts of acid | Parts of dye | Depletion point* |
|---|---|---|
| 0.045 | 0.005 | Not observed |
| 0.068 | 0.0075 | 100 |
| 0.09 | 0.01 | 80 |
| 0.27 | 0.03 | 73 |
| 0.45 | 0.05 | 70 |
| 0.9 | 0.1 | 66 |
| 1.35 | 0.15 | 62 |
| 1.8 | 0.2 | 57 |
| 2.7 | 0.3 | 50 |
| 3.6 | 0.4 | 45 |

*percentage of the total fragrance evaporated.

Example 2

Examples of Compositions for a Plug-In Air Freshener

Composition (A)

An air freshener composition was prepared by mixing the following ingredients in the indicated amounts:

| Ingredients | Parts by weight |
|---|---|
| Fragrance1) | 9600 |
| Amorphous fumed silica gel1) | 400 |
| PERGASCRIPT RED I-6B ®1) | 5 |

1) As in example 1

Composition (B)

An air freshener composition was prepared by mixing the following ingredients in the indicated quantities:

| Ingredients | Parts by weigh |
|---|---|
| Fragrance1) | 960 |
| Amorphous fumed silica gel1) | 40 |
| Lauric acid | 3.6 |
| PERGASCRIPT RED I-6B ®1) | 0.4 |

1) As in example 1

General Description of the Device 5.1 grams of one of the compositions as described herein above was placed in a cartridge, one side of said cartridge being composed of BAREX® resin (origin: BP Chemicals) used as a reservoir for the fragranced composition, and the other side being a transparent semi-permeable membrane of about 150–180 microns thickness and made of an ethylene ethyl acrylate copolymer, said membrane being used for the diffusion of the fragrance. The cartridge was then placed in an electric heating unit (plug-in type air freshener) to allow diffusion of the fragrance. The unit was plugged in a 120-volt outlet, heating the cartridge to 37° C.

Note that the cartridge does not necessarily need heat to diffuse the fragrance. Using a more permeable membrane can regulate amount of heat required. It is possible to use a membrane that is permeable enough to allow diffusion of the fragrance at room temperature.

Observations were made over a 45-day time period. Over this period of time, color change and diffusion of fragrance were recorded.

Results for Composition (A)

As shown in the following table, such a composition is able to display a clear change of color after 29 days, or at 67% depletion of the fragrance, to indicate when the air freshener starts to become inefficient in use.

| Time (days) | Depletion* | Observations |
|---|---|---|
| 0–19 | 0 to 50 | no color change |
| 20–25 | 51 to 66 | a very slight pink hue started to develop |
| 26 | 67 | a distinct magenta color was evident |
| 27–45 | 67 to 92 | color became darker and change more obvious |

*Percentage of the total fragrance evaporated.

Results for Composition (B)

As shown in the following table, such a composition is able to display a clear change of color after 30 days, or at 68% depletion of the fragrance, to indicate when the air freshener started to become inefficient in use.

| Time (days) | Depletion* | Observations |
|---|---|---|
| 0–19 | 0 to 52 | no color change |
| 20–25 | 53 to 67 | a very slight pink hue started to develop |
| 26 | 68 | a distinct magenta color was evident |
| 27–45 | 69 to 92 | color became dark and change more obvious** |

*Percentage of the total fragrance evaporated.
**During this period color became much darker then the experiments without acid

Example 3

Examples of Compositions for a Gel Type Air Freshener

Into a mixture of 1.700 grams of functionalized polymer (LITHINE N4-B-10MA) and 6.400 grams of perfume (the fragrance is same as in example 1) were dissolved 0.070 grams of PERGASCRIPT RED®. Then was prepared a second solution by admixing 1.700 grams of perfume and 0.20 grams cross-linking agent (JEFFAMINE D-400).

A gel type air freshener composition was prepared by admixing, with a good stirring, the two solutions. Then, 5 grams of this composition was left to stand into a circular container that is 5 cm in diameter. The composition gellified after approximately 30 minutes.

As shown in the following table, such a composition is able to display a clear change of color after 29 days, or at 57% depletion of the fragrance, to indicate when the air freshener started to become inefficient in use.

| Time (days) | Depletion* | Observations |
| --- | --- | --- |
| 0–24 | 0–53 | No color change |
| 24–28 | 53–56 | a very slight pink hue started to develop |
| 29 | 57 | a distinct magenta color was evident |
| after 30 | after 57 | color became dark and change more obvious |

*Percentage of the total fragrance evaporated.

What is claimed is:

1. A composition capable of indicating by color change when a consumer article capable of dispensing a volatile material containing, or associated with, said composition has become ineffective in use, said composition comprising:
   a) a volatile liquid component,
   b) a non-volatile component selected from the group consisting of i) the oxides or hydroxides of the metals in group III or IV of the periodic table; and ii) a polymer obtainable by reaction, in the presence of the volatile liquid component, of a functionalized polymer with a cross-linking agent having one or more complementary functional groups, said functionalized volume being selected from the group consisting of a functionalized liquid volume and a copolymer of ethylene and maleic anhydride; and
   c) a dye that changes color as a function of the medium in which it is incorporated.

2. A composition according to claim 1, wherein the dye is selected from the group consisting of diaryl phthalide and their indole derivatives, diaryl sulphophthalein and fluorans.

3. A composition according to claim 2, wherein the dye is selected from the group consisting of N-[9-(2-carboxyphenyl)-6-(diethylamino)-3H-xanthen-3-ylidene]-N-ethyl-ethamine free base, 3,3-bis(1-octyl-2-methylindol-3-yl) phthalide, 3,3-bis(1-ethyl-2-methylindol-3-yl)bis (1-butyl-2-methylindol-3-yl) phthalide, 3,3-bis(1-pentyl-2-methylindol-3-yl) phthalide, 3,3-bis( 4-dimethylaxninophenyl)-6-dimethyl amino phthalide, 2'-(bisphenylmethyl) amino-6-(diethylamino)spiro-(isobenzofuran-1(3H), 9'-(9H)xanthen)-3-one, 3-(4-diethylamino) phenyl-3-(di(4-octyl) phenylamino)t-(3H)-isobenzofuranone and 2-anilino-3-methyl-6-diethyl-amino fluoran.

4. A composition according to claim 1, wherein the functionalized polymer is a liquid functionalized polymer of maleinized polybutadiene or maleinized polyisoprene.

5. A composition according to claim 1, wherein the non-volatile component is selected from the group consisting of the polymers obtained by the reaction as defined in claim 1 wherein the functionalized polymer is a functionalized liquid polymer selected from the group consisting of maleinized polyisoprene of molecular weight 200000–500000 and maleinized polybutadiene of molecular weight 5000–20000.

6. A composition according to claim 1, wherein the non-volatile component is selected from the group consisting of the polymers obtained by the reaction as defined in claim 1 wherein the cross-linking agent is selected from the group consisting of a dihydroxypolybutadiene, an ethoxylated primary amine, an alkylpropyldiamine having an ethoxylated higher aliphatic chain, an alkylpropyldiamine having a propoxylated higher aliphatic chain, diethanolamine, diethylenetriamine, a polyoxy-alkylenediamine or -triamine, and a cocoamine having 5 ethylene oxide units.

7. A composition according to claim 6, wherein the cross-linking agent is an oleylamine having 2 ethylene oxide units per molecule or a cocoamine having 5 ethylene oxide units per molecule.

8. A composition according to claim 1, wherein the non-volatile component is selected from the group consisting of silica gel, alumina or $MgSiO_4$.

9. A composition according to claim 1, wherein the volatile liquid phase is a perfume, a deodorizing or sanitizing agent or an insect repellent.

10. A composition according to claim 9, wherein the volatile liquid phase is a perfume.

11. A composition according to claim 9, wherein the volatile liquid contains less than 1% of water.

12. A composition capable of indicating by color change when a consumer article capable of dispensing a volatile material containing, or associated with, said composition has become ineffective in use, said composition comprising:
   a) a volatile liquid component,
   b) a non-volatile component selected from the group consisting of i) the oxides or hydroxides of the metals in group III or IV of the periodic table; and ii) a polymer obtainable by reaction, in the presence of the volatile liquid component, of a functionalized polymer with a cross-linking agent having one or more complementary functional groups, said functionalized polymer being selected from the group consisting of a functionalized liquid polymer and a copolymer of ethylene and maleic anhydride;
   c) a dye that changes color as a function of the medium in which it is incorporated; and
   d) an acidic compound.

13. A composition according to claim 12, wherein the acidic compound is lauric, stearic, myristic, palmitic acid or diphenol-dimethyl-methane.

14. A consumer article in the form of a volatile material dispenser containing, or associated with, a composition according to claim 1.

15. A volatile material dispenser according to claim 14, in the form of an air freshener, a diaper pail freshener, a car freshener, a closet freshener, a cat litter box freshener, a shoes freshener, a garbage pail freshener or an insecticide or an insect repellent device.

16. A volatile material dispenser according to claim 15, in the form of a membrane-"plug-in" air freshener.

17. A volatile material dispenser according to claim 15, in the form of a gel type air freshener.

18. The composition of claim 1 wherein the dye is initially colorless and then changes to color that is clearly distinct from that of the dye when dissolved in the phase.

19. The consumer article of claim 10 which is initially sealed to prevent diffusion of the volatile liquid wherein a consumer can activate the article by removing the seal.

20. The composition of claim 1, wherein the consumer article is in the form of an air freshener, a diaper pail freshener, a car freshener, a closet freshener, a cat litter box freshener, a shoes freshener, a garbage pail freshener or an insecticide or an insect repellent device.

21. The composition of claim 12, wherein the consumer article is in the form of an air freshener, a diaper pail freshener, a car freshener, a closet freshener, a cat litter box freshener, a shoes freshener, a garbage pail freshener or an insecticide or an insect repellent device.

* * * * *

UNITED STATES PATENT AND TRADEMARK OFFICE
CERTIFICATE OF CORRECTION

PATENT NO. : 7,033,990 B2  
APPLICATION NO. : 10/438936  
DATED : April 25, 2006  
INVENTOR(S) : Dundale et al.

It is certified that error appears in the above-identified patent and that said Letters Patent is hereby corrected as shown below:

Title page,
Item [63], Related U.S. Application Data, after "filed on Nov. 14, 2001," change "which" to -- and --.

Column 9,
Line 43, after "said functionalized" change "volume" to -- polymer --.
Line 45, after "liquid" change "volume" to -- polymer --.
Line 51, after "their indole derivatives, dairyl" change "sulphophthalein" to -- sulphophthaleins --.
Lines 57-58, after "phthalide, 3,3-bis(1-ethyl-2-methylindol-3-yl)" delete "bis(1-butyl-2-methylindol-3-yl)"; and after "phthalide, 3,3-bis" insert -- (1-butyl-2-methylindol-3-yl) phthalide, 3,3-bis --.
Line 59, after "dol-3-yl) phthalide, 3,3-bis" change "(4-dimethylaxninophenyl)" to -- (4-dimethylaminophenyl) --.

Signed and Sealed this

Eleventh Day of July, 2006

JON W. DUDAS  
*Director of the United States Patent and Trademark Office*